//  US 9,809,818 B2

United States Patent
Han et al.

(10) Patent No.: US 9,809,818 B2
(45) Date of Patent: Nov. 7, 2017

(54) PEPTIDE NUCLEIC ACID OF PORCINE REPRODUCTIVE AND RESPIRATORY SYNDROME VIRUS AND USES THEREOF

(71) Applicant: Jianbao Han, Jiangsu (CN)

(72) Inventors: Jianbao Han, Nanjing (CN); Bo Liu, Nanjing (CN)

(73) Assignee: Jianbao Han, Nanjing (CN)

( * ) Notice: Subject to any disclaimer, the term of this patent is extended or adjusted under 35 U.S.C. 154(b) by 13 days.

(21) Appl. No.: 15/307,003

(22) PCT Filed: Dec. 10, 2012

(86) PCT No.: PCT/CN2012/001675
§ 371 (c)(1),
(2) Date: Oct. 27, 2016

(87) PCT Pub. No.: WO2013/189004
PCT Pub. Date: Dec. 27, 2013

(65) Prior Publication Data
US 2017/0218370 A1    Aug. 3, 2017

(30) Foreign Application Priority Data

Jun. 20, 2012 (CN) .......................... 2012 1 0205068

(51) Int. Cl.
*C07H 21/00*    (2006.01)
*C12N 15/113*   (2010.01)

(52) U.S. Cl.
CPC ...... *C12N 15/1131* (2013.01); *C12N 2310/11* (2013.01); *C12N 2310/3181* (2013.01); *C12N 2320/32* (2013.01)

(58) Field of Classification Search
CPC ................... C12N 15/1131; C12N 2310/3181
See application file for complete search history.

(56) References Cited

FOREIGN PATENT DOCUMENTS

| CN | 101748125 A | 6/2010 |
|---|---|---|
| CN | 102296069 A | 12/2011 |
| CN | 102796181 A | 11/2012 |

OTHER PUBLICATIONS

Cao Su-Fang et al. "Construction and Identification of siRNA Expression Vector Targeting Nucleocapsid Protein N gene of PRRSV". Agricultural Science & Technology, 2009, 10(4):171-174.
He Yun-Xia, et al "Selection and inhibitory effect analysis of SiRNAs Specific to ORF2-4 of Porcine Reproductive and Respiratory Syndrome Virus." Chinese Journal of Biotechnology, vol. 23, No. 5, Sep. 2007.
Luessen H L, de leeuw B J, Lang emeyer M, et al. Mucoadhesive polymers in peroral peptide drug delivery. Ö. carbomer and chitosan improve the absorption of the peptide drug buserelin in vivo [ J]. Pharm Res, 1996, 13(11): 1668-1172.
Kotze A F, Luessen H L, de Leeuw B J, et al. Comparison of the effect of different chitosan salts and N-tr-l methyl chitosan chloride on the permeability of intestinal epithelial cells [J]. J Control Release, 1998, 51 (1): 35-46.
T hanoo B C, Sunny M C, Jayakrishnan A. Crosslinked chitosan microspheres: preparation and evaluation as a matrix for the controlled release of pharmaceuticals [J]. J Pharm Pharmacol, 1992, 44(4): 283-286.
Portero A, RemunanLo pez C, Criado M T, et al. Reacetylated chitosan microspheres for controlled delivery of antimicrobial agents to the gastric mucosa [J]. J Microencapsul, 2002, 19(6): 797-809.

*Primary Examiner* — Brian Whiteman
(74) *Attorney, Agent, or Firm* — Treasure IP Group, LLC.

(57) ABSTRACT

The present invention discloses a peptide nucleic acid for porcine reproductive and respiratory syndrome virus (PRRSV) and use thereof. The peptide nucleic acid of the present invention is selected from any one or more from the peptide nucleic acids having a) a nucleic acid sequence of Sequence 1 as shown in the Sequencing List; b) a nucleic acid sequence of Sequence 2 as shown in the Sequencing List; c) a nucleic acid sequence of Sequence 3 as shown in the Sequencing List; and d) a nucleic acid sequence of Sequence 3 as shown in the Sequencing List. The peptide nucleic acid of the present invention has no toxic side effect and no resistance, is able to specifically directly inhibit the replication of PRRSV, has a good anti-viral effect, and suffers no food safety problems including drug residue and others.

7 Claims, No Drawings

SEQUENCE LISTING

```
<160> NUMBER OF SEQ ID NOS: 16

<210> SEQ ID NO 1
<211> LENGTH: 21
<212> TYPE: RNA
<213> ORGANISM: Artificial Sequence
<220> FEATURE:
<223> OTHER INFORMATION: synthetic

<400> SEQUENCE: 1
aauaugagag cuguuguugu u                                           21
```

<210> SEQ ID NO 2
<211> LENGTH: 21
<212> TYPE: RNA
<213> ORGANISM: Artificial Sequence
<220> FEATURE:
<223> OTHER INFORMATION: synthetic

<400> SEQUENCE: 2
uuaaguuaua aaucaacuga a                                              21

<210> SEQ ID NO 3
<211> LENGTH: 21
<212> TYPE: RNA
<213> ORGANISM: Artificial Sequence
<220> FEATURE:
<223> OTHER INFORMATION: synthetic

<400> SEQUENCE: 3
aauggaaaac gccaaaagca c                                              21

<210> SEQ ID NO 4
<211> LENGTH: 21
<212> TYPE: RNA
<213> ORGANISM: Artificial Sequence
<220> FEATURE:
<223> OTHER INFORMATION: synthetic

<400> SEQUENCE: 4
ucagaaagau caaaaggugc a                                              21

<210> SEQ ID NO 5
<211> LENGTH: 21
<212> TYPE: DNA
<213> ORGANISM: Artificial Sequence
<220> FEATURE:
<223> OTHER INFORMATION: probe
<220> FEATURE:
<221> NAME/KEY: modified_base
<222> LOCATION: (1)..(1)
<223> OTHER INFORMATION: join to FAM
<220> FEATURE:
<221> NAME/KEY: modified_base
<222> LOCATION: (21)..(21)
<223> OTHER INFORMATION: join to TARAM

<400> SEQUENCE: 5
tcccggtccc ttgcctctgg a                                              21

<210> SEQ ID NO 6
<211> LENGTH: 21
<212> TYPE: RNA
<213> ORGANISM: Artificial Sequence
<220> FEATURE:
<223> OTHER INFORMATION: synthetized

<400> SEQUENCE: 6
aauaugagag cuguuguugu u                                              21

<210> SEQ ID NO 7
<211> LENGTH: 21
<212> TYPE: RNA
<213> ORGANISM: Artificial Sequence
<220> FEATURE:
<223> OTHER INFORMATION: synthesized

<400> SEQUENCE: 7

```
uuaaguuaua aaucaacuga a                                              21

<210> SEQ ID NO 8
<211> LENGTH: 21
<212> TYPE: RNA
<213> ORGANISM: Artificial Sequence
<220> FEATURE:
<223> OTHER INFORMATION: synthesized

<400> SEQUENCE: 8
aaugacaaag caaaucagcg c                                              21

<210> SEQ ID NO 9
<211> LENGTH: 21
<212> TYPE: RNA
<213> ORGANISM: Artificial Sequence
<220> FEATURE:
<223> OTHER INFORMATION: synthesized

<400> SEQUENCE: 9
uggaaaacgc caaaagcacc u                                              21

<210> SEQ ID NO 10
<211> LENGTH: 21
<212> TYPE: RNA
<213> ORGANISM: Artificial Sequence
<220> FEATURE:
<223> OTHER INFORMATION: synthesized

<400> SEQUENCE: 10
aauggaaaac gccaaaagca c                                              21

<210> SEQ ID NO 11
<211> LENGTH: 21
<212> TYPE: RNA
<213> ORGANISM: Artificial Sequence
<220> FEATURE:
<223> OTHER INFORMATION: synthesized

<400> SEQUENCE: 11
ucagaaagau caaaaggugc a                                              21

<210> SEQ ID NO 12
<211> LENGTH: 22
<212> TYPE: DNA
<213> ORGANISM: Artificial Sequence
<220> FEATURE:
<223> OTHER INFORMATION: Primer

<400> SEQUENCE: 12
aaatggggct tctccgggtt tt                                             22

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
tcagctgtgc cagatgctgg                                                20

<210> SEQ ID NO 14
<211> LENGTH: 24
<212> TYPE: DNA
<213> ORGANISM: Artificial Sequence
```

```
<220> FEATURE:
<223> OTHER INFORMATION: internal reference

<400> SEQUENCE: 14
tgactgacta cctcatgaag atcc                                              24

<210> SEQ ID NO 15
<211> LENGTH: 23
<212> TYPE: DNA
<213> ORGANISM: Artificial Sequence
<220> FEATURE:
<223> OTHER INFORMATION: internal reference

<400> SEQUENCE: 15
tctccttaat gtcacgcacg att                                               23

<210> SEQ ID NO 16
<211> LENGTH: 24
<212> TYPE: DNA
<213> ORGANISM: Artificial Sequence
<220> FEATURE:
<223> OTHER INFORMATION: probe
<220> FEATURE:
<221> NAME/KEY: modified base
<222> LOCATION: (1)..(1)
<223> OTHER INFORMATION: link to o FAM
<220> FEATURE:
<221> NAME/KEY: modified base
<222> LOCATION: (24)..(24)
<223> OTHER INFORMATION: link to o TARAM

<400> SEQUENCE: 16
cggctacagc ttcaccacca cggc                                              24
```

PEPTIDE NUCLEIC ACID OF PORCINE REPRODUCTIVE AND RESPIRATORY SYNDROME VIRUS AND USES THEREOF

CROSS REFERENCE TO RELATED APPLICATION

This application is a National Phase application of, and claims priority to, PCT Application No. PCT/CN2012/001675, filed on Dec. 10, 2012 entitled "PEPTIDE NUCLEIC ACID OF PORCINE REPRODUCTIVE AND RESPIRATORY SYNDROME VIRUS AND USES THEREOF", which claims priority to Chinese Application No. 201210205065.0, filed on Jun. 20, 2012. Both the PCT Application and Chinese Application are incorporated herein by reference in their entireties.

BACKGROUND

Technical Field

The present invention relates to a peptide nucleic acid of porcine reproductive and respiratory syndrome virus (PRRSV) and use thereof.

Related Art

Porcine reproductive and respiratory syndrome (PRRS) is a viral infectious disease caused by PRRS virus (PRRSV) and mainly characterized by swine reproductive disorder and Porcine Respiratory Disease Complex (PRDC). In 1987, PRRSV was initially found in the midwestern United States, and spread rapidly throughout the whole country, and then widespread around the world in a few years, causing a heavy economic loss to the swine industry. In 1992, the virus was officially termed as PRRSV on the International Conference of Virology. In 1996, PRRSV was initially isolated by Guo Baoqing et al from pigs with suspected PRRSV infection in China, thus confirming the existence of this virus in China. At present, PRRSV has become one of the vital pathogens causing infectious diseases to swine in China. The diseases are designated as category B infectious disease by the Office International Des Epizooties (OIC), and also category II infectious disease in China. Among them, high 2 pathogenic swine of blue ear disease is a class of infectious diseases.

The latency of PRRS is generally 3-24 days. Once present in the swine herd, PRRSV spreads rapidly, and the serum positive rate can generally be up to 85-95% in 2-3 months. The infected pigs have the symptoms of poor mental state, poor appetite or loss of appetite, elevated body temperature of 40.2-42.0° C., cough, and respiratory distress. After attack by the disease, the pigs at various ages show breathing difficulty, but the specific symptoms are not completely the same.

After being infected, the sows initially show anorexia, elevated temperature, shortness of breath, runny nose and other symptoms similar to the flu; a few (2%) show cyanosis of ends of the limbs, tail, nipple, vagina and ear tip, and cyanosis of the ear tip is mostly common; and very few sows may suffer from diarrhea. Finally, the paralyzed limbs and other symptoms may occur and usually last 1-3 weeks, and the sows may eventually died of failure. Sows in early pregnancy experience abortion, sows in middle pregnancy experience stillbirth, mummification, or give birth to weak or abnormal fetus, and sows in breast feeding fail to lactation post partum, causing the sucking pigs to starve to die.

After being infected, the boars show cough, sneezing, depression, inappetence, shortness of breath, movement disorders, decreased sexual desire, decreased semen quality, and less ejaculation.

After being infected, the growing finishing pigs and weaned piglets mainly show anorexia, lethargy, cough, and dyspnea, some pigs have swollen eyes, conjunctivitis and diarrhea, some weaned piglets have diarrhea, arthritis, red ears, and skin spots. Sick pigs often die of secondary infection with pleurisy, streptococcicosis, and asthma. If there is no secondary infection, the growing finishing pigs may be recovered.

After being infected, the suckling piglets have the symptoms of coarse hair, depression, dyspnea, asthma or ears cyanosis. Some have bleeding tendency, subcutaneous plaques, arthritis, sepsis and other symptoms, and the mortality rate is as high as 60%. The mortality of the piglets before weaning is increased, and the peak time usually lasts for 8-12 weeks. Once infected with the virus in the embryonic period, the newborns die at birth a few days after death, and the mortality rate is as high as 100%.

PRRSV is a member of the genus Arterivirus, which is an enveloped, non-segmented, single-stranded, positive-sense RNA virus. The virus is of spherical shape having a diameter of 50-65 nm, and has a nucleocapsid that is a symmetric icosahedron and has fine fibrous protrusions on surface thereof. The virus includes two serotypes, that is, the North American type, and the European type, and the strain isolated in China is the North American type. The genome has a full length of about 15 kb, and comprises 8 open reading frames (ORFs), in which adjacent reading frames are partially overlapped. An about 12 kb-long ORF1 is present at the 5' terminus. ORF1 comprises ORF1a and ORF1b having 16 nucleotides overlapped, and accounts for 80% of the whole genome, thus giving rise to a non-structural protein (encoding RNA replicase and polymerase). The encoding region of ORF1a includes some hydrophobic regions, a putative serine protease region, and a cysteine-rich region. The leader sequence immediately adjacent to the initiation codon of ORF1a has two hairpin structures. The encoding initiation region of ORF1a has a core sequence of 5'-UAACCAU-3', and is highly conserved. ORF1b comprises 4 domains: (1) a motif sequence of polymerase; (2) a zinc finger region rich in cysteine and histidine; (3) a motif sequence of helicase; and (4) a conserved region with unknown functions. A 5 non-coding region (NCR) of about 180-220 nucleotides in length is present upstream of ORF1, which is highly conserved and functions to initiate the translation of subgenomic mRNAs as a 5-terminal leader sequence. The gene expression pattern of PRRSV is expression by producing 6 subgenomic mRNAs that have a consensus leader sequence derived from 5 NCR of the viral genome, and share a common 3 nested structure. 6 encoding frames (ORF2-7) are present at the 3 terminus, which encode the viral structural proteins. The envelope proteins encoded by ORF2-ORF5 are GP2, GP3, GP4, and GP5 respectively, the membrane matrix protein encoded by ORF6 is the M protein, and the nucleocapsid protein encoded by ORF7 is the N protein. The termination codon of ORF7 is followed by a 3 non-coding region containing a Poly(A) tail, i.e. a conserved sequence of about 10 nucleotides in length, which is a region recognized and bound by an enzyme during viral replication, to initiate the synthesis of a negative stranded RNA. Among the structural proteins of PRRSV, GP5, M, and N are the primary structural proteins, and GP2a, GP3, GP4 and E are the secondary structural proteins, which are present at a low level in virions, and the function of which are less studied. It is confirmed by Welch et al that ORF2 and ORF4 deleted infectious molecular clones of PRRSV can be rescued in cell lines providing the correspondingly deleted proteins, to produce infectious virions. Whether GP3 is present in the virion is a matter in dispute. In LDV, GP3 is proved to be a non-structural, soluble glycoprotein that can be secreted from infected cells. In EAV, GP3 is proved to be assembled into virions in the form of structural protein. Both of the two cases may occur to PRRSV. The GP3 protein of European-type PRRSV LV isolate is proved to be present in the virion, and the GP3 protein of North American type isolate is proved to be present in the form of secretion (sGP3). The E protein is a newly identified small non-glycosylated hydrophobic envelope protein, which has a potential N-terminal N-myristoylation site and a tyrosine kinase II phosphorylase site, a central hydrophobic domain, and a hydrophilic C terminus rich in alkaline residues, and is present in all arteritis virions. The translation initiation codon of mutant E protein causes the infectious molecular clone of EAV to lose the infectivity.

A wide range of variations exist in the nucleotide sequence of PRRSV isolate. Substitution, insertion, deletion or gene recombination may occur to PRRSV at the nucleotide and amino acid levels. Studies show that variant blue-ear pig disease virus may cause "high fever" of swine, which is termed as "highly pathogenic blue ear disease of swine" for discrimination from ordinary blue ear disease. Compared with the blue-ear pig disease virus prevalent in China in 1996, the virulence and pathogenicity of the variant strain are significantly boosted. In 2006, in pig farms in some southern provinces of China, swine "high fever" syndrome broke out, in which the infected pigs mainly show the clinical characteristics such as high body temperature, high incidence and high mortality. Subsequently, it is confirmed through study that the main pathogen of the disease is PRRSV with deletion variation. The genetic variations of GP5 protein of PRRSV occurring from 1996 to 2006 in mainland of China are analyzed by Tong Guangzhi et al, and the results show that the PRRSV strains occurring from 1996 to 2006 in mainland of China are highly homogenous to strain VR22332 (representative strain of North American type virus) in terms of the amino acid sequence (85.5%-99.0%), and lowly homogenous to strain LV (representative strain of European type virus) (53.5%-57.0%). This suggests that the strains prevalent in China are all North American type, and can be classified into two subgroups that are far in inheritance relationship. All the strains of subgroup I have variations at the antibody binding site of the primary antigen neutralization epitope of the virus, and the subgroup II is highly conserved at this site. Although the genome of PRRSV has wide genetic variations, the M and N proteins are relatively conserved in all strains. The M protein gene is the most conserved, and the GP5 gene has the highest sequence difference.

ORF1 encodes the viral replicase. After processing, the oligomeric protein encoded by ORF1a forms 6 non-structural proteins (Nsp1α, Nsp1β, and Nsp2-Nsp5), where Nsp2 varies highly between the North American type and European type strains, and the homogeneity of amino acid sequence is merely 32%. The oligomeric protein encoded by ORF1b is about 1463 amino acids long, and cleaved by the protease encoded by ORF1a, to form 4 proteins, that is, RdRp, CP2, CP3, and CP4. GP2 is a glycoprotein encoded by ORF2, and has a molecular weight of 29-30 ku. The PRRSV GP2 of both gene types comprises 2 apparent hydrophobic peaks and 2 inferred N-glycosylation sites. GP3 is a glycoprotein encoded by ORF3, which has a molecular weight of 27-29 ku, is one of the proteins having the worst conservation among the strains of PRRSV, and has an inferred homogeneity of amino acid sequence of 54%-60% between the North American type and European type strains, with most of the variations occurring at the N terminus. GP4 is a glycosylated envelope protein encoded by ORF4, which has a molecular weight of 19-20 ku, comprises 4 glycosylation sites, and has a highly hydrophobic region at the N and C terminus. GP5 is a glycosylated envelope protein encoded by ORF5, which is also referred to as E protein, and has a molecular weight of about 22.4 ku; the GP5 proteins derived from the North American type and European type isolates comprise 200 and 201 amino acids respectively, have 6 antigenic determinants, and can induce an organism to produce specific neutralizing antibodies. The M protein is a membrane matrix protein encoded by ORF6 and has a molecular weight of 18-19 ku; and the amino acid sequences of the M protein between the North American type and European type strains are inferred to be the most conserved, comprise 173 and 174 amino acids, and have a homogeneity of 78-81%. The N protein is a nucleocapsid protein encoded by ORF7, which has a molecular weight of 14-15 ku, and is the smallest primary structural protein in PRRSV. The N protein of the North American type and European type PRRSV strains comprises 123 and 128 amino acids respectively, and the N protein of the European type strain has two more amino acid extensions at the N and C terminus than the North American type strain, which are STAPM and SQGAS respectively.

Antisense nucleic acid is a fragment of naturally occurring or artificially synthesized nucleotide sequence that is complementary to a sequence of a target gene (mRNA or DNA), and specifically binds to the viral target gene by base pairing to form a hybrid molecule, thus playing a role in the regulation of target gene expression at the level of replication, transcription, or translation, or in the induction of RNase H to recognize and cleave mRNA such that the function of mRNA is lost.

The antisense nucleic acid includes antisense RNA and antisense DNA, and is characterize by convenient synthesis, simple sequence design, easy modification, high selectivity, and high affinity. As a new anti-viral and anti-tumor agent, the antisense nucleic acid arouses a revolution in the field of pharmacology, that is, new reactions post drug-receptor binding are initiated by a new drug receptor mRNA through the new binding pattern to the receptor (Watson-Crick crossing), including: (1) degradation of the target RNA mediated by RNase H; and (2) inhibition on the DNA replication and transcription and post-transcriptional processing and translation, etc. It is believed that the antisense oligonucleotide (ODNs) therapy is more specific than the conventional drug therapies. Since the late 1970s, the antisense nucleic acid drugs have went out of the laboratory, and put into practical clinical use in the over three decades of years. The antisense therapy receives great attention especially after the first antisense nucleic acid drug Fomivirsen is approved by FDA.

The mechanism of action of antisense nucleic acids is that based on the principle of base pairing, it is involved in the regulation of relevant gene expression by binding to the target RNA through base pairing. The modes of action may include the following. (1) The anti-sense RNA is bound to the viral mRNA, to from a complementary duplex, thus blocking the binding of ribosome to viral mRNA, and inhibiting the translation of viral mRNA into proteins. (2) The anti-sense DNA can form a triple helix nucleic acid with the target gene, and regulate the transcription of a gene by acting on the transcript, enhancer and primer region controlling the gene transcription. (3) The binding of the anti-sense nucleic acid to the viral mRNA can prevent the transport of the mRNA to cytoplasm. (4) After the binding of the antisense nucleic acid to the viral mRNA, the mRNA are more easily recognized and degraded by the nuclease, thus greatly reducing the half life of mRNA. The four pathways of action may all be embodied as the inhibition or regulation for viral gene expression, and the regulation is highly specific.

The antisense nucleic acid recognizes the targeting gene based on the principle of base complementation and pairing. Theoretically, for example, the chromosome of animal cells has about several billions of pairs of bases. If the number of the 4 bases (A, G, C, and T) are substantially the same and distributed at random in the whole gene, then the antisense nucleic acid of greater than 17 bases is unlikely to hybridize to a non-target gene according to the principle of statistics. Therefore, the binding of the antisense nucleic acid molecule of greater than 17 bases to the target gene is unique, such that the antisense nucleic acid is highly specific.

Studies show that a copy of gene in the cell can produce 200-300 mRNAs, from which 100,000 biologically active protein molecules are translated. The conventional drugs mainly act on several sites on a domain of the protein molecule having biological functions. Actually, the protein structure is very complex and the spatial structure of active proteins in an organism is versatile. It is difficult to achieve a desirable effect by controlling the dynamics and overall functions of the target molecules via the limited several sites on which the conventional drugs act. Therefore, the limitation of the conventional drugs is obvious. Several dozens to hundreds of protein may be translated from the mRNA, and the target gene is directly regulated by the antisense nucleic acid at the mRNA level, which means that the efficacy of the conventional drugs is increased by several dozens to hundreds of times. It can be seen that the regulation by antisense nucleic acid is quite economic and reasonable.

Toxicological research shows that the antisense nucleic acid has an extremely low toxic in vivo. Although the antisense nucleic acid may remain in vivo for a long or short period of time, it is finally removed by degradation, through which the hazard caused by integration of an exogenous gene into the chromosome of a host in a transgenic therapy is avoided. Compared with the conventional drugs, the antisense nucleic acid drugs have the advantages of high specificity, high efficacy, and low toxic effect, and are useful in the inhibition of tumor growth and viral replication. Currently, numerous drugs become available in American and European markets, and additional 30 antisense nucleic acid drugs are under preclinical study or under phases I, II, and III trial after development.

Due to the large existence of exonucleases in animals, the antisense nucleic acid is quickly degraded and loses the activity if it is not chemically modified. At present, the antisense nucleic acid may be chemically modified through many methods, for example, the common modification of an antisense nucleic acid with phosphorthioate and 2'-methoxy. Moreover, the modification of drugs with phosphorthioate is well studied, and it can effectively resist the degradation by nuclease, and contributes to the activity of the nucleaseRase H. Currently, this modification method is successfully used with the antisense nucleic acid drugs in clinic. However, these are merely modification method for the first generation of antisense nucleic acids. With the development and progression of technologies, new routes and methods of modification will be developed, which allows the research of the second and third generations of antisense nucleic acids to be carried out. Among them, the modification of peptide nucleic acids receives the greatest attention.

Peptide nucleic acids (PNAs) are new analogs of DNA that have neutral amide bonds in the backbone, and can specifically target the groove in DNA. The structural component is N(2-aminoethyl)-glycine, and the bases are attached via methylenecarbonyl to the amino N of the backbone. PNAs are the second generation of antisense nucleic acids.

OBJECT OF THE INVENTION

PRRSV is one of the vital pathogens that cause great hazards to the swine industry worldwide at present. The pig density is large in the intensive production. PRRSV is highly infectious and mainly characterized by swine reproductive disorder and respiratory symptoms of growing pigs, thus causing a heavy economic loss to the swine industry. By far, there are no effective measures for preventing the disease, and the development of new technologies for preventing and treating PRRSV infection becomes particularly urgent. Furthermore, PRRSV primarily invades the macrophage system mainly including alveolar macrophages of pigs, such that the infected pigs are low in immunity, thereby causing immunosuppression. There is no substantial breakthrough in vaccine research. In the present invention, the peptide nucleic acid technology and the antisense nucleic acid technology are combined, and used for preventing and treating related diseases caused by PRRSV infection.

An object of the present invention is to provide a peptide nucleic acid of PRRSV and use thereof.

SUMMARY OF THE INVENTION

The present invention provides a peptide nucleic acid, which is selected from any one or several of the peptide nucleic acids having a) a nucleic acid sequence of Sequence 1 as shown in the Sequencing List:

(SEQ ID NO: 1)
5'-AAUAUGAGAGCUGUUGUUGUU-3';

b) a nucleic acid sequence of Sequence 2 as shown in the Sequencing List:

(SEQ ID NO: 2)
5'-UUAAGUUAUAAAUCAACUGAA-3';

c) a nucleic acid sequence of Sequence 3 as shown in the Sequencing List:

(SEQ ID NO: 3)
5'-AAUGGAAAACGCCAAAAGCAC-3';

and d) a nucleic acid sequence of Sequence 4 as shown in the Sequencing List:

(SEQ ID NO: 4)
5'-UCAGAAAGAUCAAAAGGUGCA-3'.

The peptide nucleic acid may be a peptide nucleic acid modified with chitosan.

The peptide nucleic acid of the present invention is useful in the preparation of drugs of PRRSV.

A drug of PRRSV, that is, a peptide nucleic acid formulation, has the peptide nucleic acid as an active ingredient.

The formulation is in the form of colon specific controlled-release microcapsule preparation, injectable lyophilized preparation or orally taken water-soluble granules.

The formulation further comprises a pharmaceutically acceptable carrier or excipient.

Stability analysis of the peptide nucleic acid preparation according to the present invention High temperature: Sterilization for 20 min with flow of high-temperature steam at 105° C., without affecting its biological activity.

Extreme temperature: storage at 50° C. for 6 months without affecting its biological activity.

Room temperature: storage for 24 months without affecting its biological activity.

Low temperature: storage at −20° C. for 48 months without affecting its biological activity.

The peptide nucleic acid of the present invention has no toxic side effect and no resistance, is able to specifically directly inhibit the replication of PRRSV, has a good anti-viral effect, and suffers no food safety problems including drug residue and others.

DETAILED DESCRIPTION

To this end, the following technical solutions are adopted in the present invention.

PRRSV strain: strain NS-009, available from Nansen Central Laboratory of Veterinary Diagnostic techniques Research.

Cell line: MARC-145 cells, available from Nansen Central Laboratory of Veterinary Diagnostic techniques Research.

The genome of PRRSV was retrieved from the GenBank database, and sequenced by using biological software. By taking the sequence conservation, the percent G+C content, and the base distribution profile into account comprehensively, an antisense nucleic acid was designed by choosing an appropriate region therefrom. The GP-5 and M gene genes of the virus finally determined had the following antisense nucleic acid sequences.

```
GP5:
                                          (SEQ ID NO: 6)
GP5-1: 5'-AAUAUGAGAGCUGUUGUUGUU-3'

(SEQ ID NO: 7)
GP5-2: 5'-UUAAGUUAUAAAUCAACUGAA-3';
and (SEQ ID NO: 8)
GP5-3: 5'-AAUGACAAAGCAAAUCAGCGC-3'.

M:
                                          (SEQ ID NO: 9)
M-1: 5'-UGGAAAACGCCAAAAGCACCU-3'.

(SEQ ID NO: 10)
M-2: 5'-AAUGGAAAACGCCAAAAGCAC-3'.;
and (SEQ ID NO: 11)
M-3: 5'-UCAGAAAGAUCAAAAGGUGCA-3'.
```

The peptide nucleic acids having the following peptide nucleic acid sequences were artificially synthesized:

```
GP5:
                                          (SEQ ID NO: 6)
GP5-1: 5'-AAUAUGAGAGCUGUUGUUGUU-3'

(SEQ ID NO: 7)
GP5-2: 5'-UUAAGUUAUAAAUCAACUGAA-3';
and (SEQ ID NO: 8)
GP5-3: 5'-AAUGACAAAGCAAAUCAGCGC-3'

M:
                                          (SEQ ID NO: 9)
M-1: 5'-UGGAAAACGCCAAAAGCACCU-3'

(SEQ ID NO: 10)
M-2: 5'-AAUGGAAAACGCCAAAAGCAC-3';
and (SEQ ID NO: 11)
M-3: 5'-UCAGAAAGAUCAAAAGGUGCA-3'.
```

The inhibition of the peptide nucleic acid on the target viral gene was detected by using quantitative RT-PCR specific for PRRSV, and the anti-viral titer was determined by viral titer assay.

Day 1:

Plating: The MARC-145 cells, prepared at an earlier stage of digestion, were collected by centrifugation, counted, adjusted to a cell density of $1 \times 10^5$ cells/ml with a complete medium, plated in a 24-well plate, and incubated for 18-24 hrs at 37° C. in a carbon dioxide incubator.

Day 2:

The cell density was microscopically observed. When the cells were grown over to 70-80% of the area of the plate and grown well, the medium was aspirated off, 300 µl of the agents (that is, the peptide nucleic acids) to be screened were added per well, each agent having 10 wells. After incubation for 1 hr, 100 µl of PRRSV (with the infection rate being 0.01) was added. After 2 hr-adsorption, the unadsorbed viruses were washed off with a nutrient solution, then 4% FBS in DMEM medium was added, and contiuously cultured at 37° C. in 5% $CO_2$. The cytopathic effect was peridically observed after infection. 48 hrs after infection, the infected cells were repeatedly frozen and thrawed, to release the viruses, and this was used as a sample for virus detection. During experiment, a normal cell control group with no virus and peptide nucleic acid, a positive control group with virus and no peptide nucleic acid, and a negative control group with peptide nucleic acid and no virus were also set.

Days 3-5:

The protection effect of the agent for cells were observed, and the result was evaluated.

Quantitative detection by Real-time PCR

The supernatant of each treatment group was collected, and the viral RNA was extracted by using a total viral RNA extraction kit. The obtained viral RNA was reversely transcripted into cDNA, and then the viral content of the treatment group with PRRSV was detected respectively by using specific Primers. From the results after quantitative amplification, the virus titer and the inhibitory effect of each treatment group in fold differences between the PNA group and the blank control group were calculated by using statistical software.

In the present invention, PRRSV was quantitatively detected by real-time PCR using primers provided by Huang et al.

PRRSV ORF7

```
Primer ORF71:
                                    (SEQ ID NO: 12)
    5'-AAATGGGGCTTCTCCGGGTTTT-3';
and Primer ORF72:
                                    (SEQ ID NO: 13)
    5'-TCAGCTGTGCCAGATGCTGG-3'.

TaqMan probe:
                                    (SEQ ID NO: 5)
    5'FAM-TCCCGGTCCCTTGCCTCTGGA-TARAM3'.
```

β-actin as internal reference

```
Actin-F:
                                    (SEQ ID NO: 14)
    5'-TGACTGACTACCTCATGAAGATCC-3';
and Actin-R:
                                    (SEQ ID NO: 15)
    5'-TCTCCTTAATGTCACGCACGATT-3'.

Actin-Probe:
                                    (SEQ ID NO: 16)
    5'(FAM)-CGGCTACAGCTTCACCACCACGGC-(TARAM) 3'
```

Reaction system (25 μl)

| Reagent | Amount (μl) |
| --- | --- |
| 2 × One-Step RT-PCR Buffer | 12.5 |
| Ex TaqT ™ HS | 0.5 |
| PrimeScript ™ RT Enzyme Mix II | 0.5 |
| Forward PCR primer | 0.5 |
| Reverse PCR primer | 0.5 |
| Total RNA | 2 |
| RNase free dH$_2$O | 8.5 |
| In total | 25 |

Reaction Condition:
Reverse Transcription:
5 min at 42° C.
10 sec at 95° C.
PCR Amplification:
Cycles: 40
5 sec at 95° C.
30 sec at 60° C.

Viral Titer Detection

When the cytopathic effect occurred, the supernatant of each treated cell culture was collected, serially diluted 10 times to give 7 dilutions, and inoculated in 100 μL/well to MARC-145 cells pre-incubated in a 96-well plate, each sample having 3 replications. The cytopathic effect was observed, until no cytopathic effect was present in the wells. The CCID50PmL (50% cell culture infectious dose) was calculated according to the Karber method.

The inhibition rate of different peptide nucleic acids on PRRSV replication was calculated according to the formula:

Inhibition rate =

$$\frac{\text{Average copies of virus in the control group challenged} - \text{Average copies of virus in the treatment group}}{\text{Average copies of virus in the control group challenged}} \times 100\%$$

Assay of Anti-Viral Effect at Various Times

The infection with viruses and the treatment with drugs were as described above, and the anti-viral effect of GP5-1, GP5-2, GP5-3, M1, M2, and M3 was assayed following the steps above. 24, 36, 48, 60, and 72 hrs after the MARC-145 cells were infected with PRRSV strain NS-009, and 300 μl of peptide nucleic acid to be screened (diluted in complete medium) was added per well, each peptide nucleic acid having 4 parallel wells. The supernatant and cells were collected 24 hrs after treatment with the agent. The copies of PRRSV in each treatment group were quantitatively detected by Real-time PCR using a TaqMan probe, and the virus inhibition rate in the treatment group was statistically analyzed. The result is shown in Table 1.

TABLE 1

In-vitro anti-PRRSV effect of peptide nucleic acids for MARC-145 cells

| | | Virus inhibition rate | | | | |
| --- | --- | --- | --- | --- | --- | --- |
| Group | | 24 h | 36 h | 48 h | 60 h | 72 h |
| Infection and treatment group | Group GP5-1 | 55% | 67% | 76% | 77% | 82% |
| | Group GP5-2 | 62% | 69% | 70% | 75% | 76% |
| | Group GP5-3 | 25% | 39% | 40% | 42% | 43% |
| | Group M-1 | 28% | 35% | 39% | 42% | 44% |
| | Group M-2 | 57% | 69% | 73% | 78% | 85% |
| | Group M-3 | 52% | 66% | 72% | 76% | 80% |
| Virus control group | | | | 0 | | |
| Negative control group | | | | 0 | | |
| Blank control group | | | | 0 | | |

Peptide nucleic acids GPS-1, GPS-2, M-2 and M-3 are preferred.

Treatment with Drugs in Combination

On basis of the experimental results above, the screened drugs having potent anti-viral effect are used in combination, to compare the difference of the anti-viral effects between the combined agents and a single agent. After the MARC-145 cells were infected with PRRSV strain NS-009, gene drug combinations of GP-5 or M were added respectively, and a positive, a negative, and a blank control group were also set. The detection was performed by Real-time PCR, and the virus inhibition rate in each treatment group was statistically analyzed, as described above. The results are shown in Table 3.

TABLE 3

In-vitro anti-PRRSV effect of various concentrations of peptide nucleic acids for MARC-145 cells

| | | Virus inhibition rate | | | | |
| --- | --- | --- | --- | --- | --- | --- |
| Group | | 24 h | 36 h | 48 h | 60 h | 72 h |
| Infection and treatment group | GP5-1 group | 60% | 55% | 68% | 62% | 60% |
| | GP5-2 group | 50% | 57% | 58% | 62% | 64% |
| | GP5-1 + 2 group | 65% | 79% | 80% | 85% | 87% |
| | M-2 group | 47% | 49% | 53% | 58% | 55% |
| | M-3 group | 47% | 60% | 63% | 78% | 75% |
| | M-2 + 3 group | 67% | 69% | 73% | 78% | 85% |
| | GP5-1 + 2 + M-2 + 3 group | 60% | 69% | 78% | 80% | 88% |
| Virus control group | | | | 0 | | |
| Negative control group | | | | 0 | | |
| Blank control group | | | | 0 | | |

Cell Toxicity Test

The object to be detected was MARC-145 cells. 100 μl containing 5000 cells was added per well to a 96-well plate. Peptide nucleic acids at concentrations of 0.02, 0.1, 0.5, 1, 5, and 10 μm) were used, each concentration were performed in triplicate. An untreated cell control and a cell free medium control were additionally set.

After treatment, 10 μl of MTT Stock was added per well per 100 μl of medium, and continuously incubated for 4 hrs in an incubator at 37° C. Alternatively, the medium was replaced with 100 μl of fresh serum-free medium, and then MTT Stock was added.

The medium was aspirated off, 100 μl of MTT lysing agent was added per well, and the volume of the liquid in each well was kept consistent.

The absorbance (OD) was measured at 570 nm, and comparison and calculation were performed. Note: considering the accuracy, the absorbance (OD) of unreduced MTT was measured at 699 nm, which is then subtracted from $OD_{570}$.

Determination of result: cell proliferation or toxicity=$100\% \times (OD_{experiment} - OD_{background})/(OD_{control} - OD_{background})$.

$OD_{experiment}$ is the OD value of treated cells, $OD_{control}$ is the OD value of untreated cells in the control tube, $OD_{background}$ is the OD value of the cell free medium control. The change in cell proliferation or toxicity after treatment is expressed as percentage of the untreated control.

The result shows that there is no significant difference (P<0.05%) between the treatment groups with peptide nucleic acids and the control group.

Animal Test

PRRSV Strain: Strain NS-009

Laboratory animals: 100 of healthy pigs aged 25 days were determined by serological and molecular biological examinations to be negative for antigens and antibodies to swine fever virus, Porcine Circovirus, parvovirus, SRRSV, and pseudorabies virus.

Chitosan-peptide nucleic acid: peptide nucleic acid modified with chitosan through various methods well known in the art, for example, as specifically described in:

Luessen H L, de leeuw B J, Lang emeyer M, et al. Mucoadhesive polymers in peroral peptide drug delivery. Ö. carbomer and chitosan improve the absorption of the peptide drug buserelin in vivo [J]. Pharm Res, 1996, 13(11): 1 668-1172.

Kotze A F, Luessen H L, de Leeuw B J, et al. Comparison of the effect of different chitosan salts and N-tr-I methyl chitosan chloride on the permeability of intestinal epithelial cells [J]. J Control Release, 1998, 51 (1): 35-46.

T hanoo B C, Sunny M C, Jayakrishnan A. Crosslinked chitosan microspheres: preparation and evaluation as a matrix for the controlled release of pharmaceuticals [J]. J Pharm Pharmacol, 1992, 44(4): 283-286.

Portero A, RemunanLo pez C, Criado M T, et al. Reacetylated chitosan microspheres for controlled delivery of ant-i microbial agents to the gastric mucosa [J]. J Microencapsul, 2002, 19(6): 797-809.

Grouping:

Group A: chitosan-peptide nucleic acid (GP5-1+2+M-2+3) added in an amount of 50 ppm;

Group B: chitosan-peptide nucleic acid (GP5-1+2+M-2+3) added in an amount of 100 ppm;

Group C: chitosan-peptide nucleic acid (GP5-1+2+M-2+3) added in an amount of 150 ppm; and Group D: chitosan-peptide nucleic acid (GP5-1+2+M-2+3) added in an amount of 0 ppm (blank control group).

Challenge: the animals in groups A, B, C, and D were challenged by intramuscularly injecting 1 ml of viral solution (in which the dosage of the virus was $10^6$ TCID50/animal).

Time at which the chitosan-peptide nucleic acid was added: 6 days before the challenge, the animals were fed on various dosages of chitosan-peptide nucleic acid, and continuously fed for additional two weeks after challenge.

Development of Disease in Challenged Pigs:

At day 3 after challenge, pigs in the test groups successively suffered from high fever (body temperature 39-41° C.), followed by symptoms of Porcine Respiratory Disease Complex (PRDC), cyanosis of skin of the ear, stomach, and buttock, general flush, seriously reduced dietary intake of pigs, depression, and failure to stand, and died of failure about 5 days after the occurrence of the symptoms with elapse of time, if no therapeutic measures were taken.

Test Results:

1. Statistical Results of Incidence Rate

Group A: chitosan-peptide nucleic acid 50 ppm, 6 animals having symptoms of PRDC, incidence rate 24%, and protection rate 76%;

Group B: chitosan-peptide nucleic acid 100 ppm, 4 animals having symptoms of respiratory syndrome, incidence rate 16%, and protection rate 84%;

Group C: chitosan-peptide nucleic acid 150 ppm, 3 animals having symptoms of respiratory syndrome, incidence rate 12%, and protection rate 88%; and Group D: chitosan-peptide nucleic acid 0 ppm, 23 animals having symptoms of respiratory syndrome, and incidence rate 92%.

Observation on Lesions of Lymph Nodes by Dissection and Viral Load Test 5 days after challenge, compared with the treatment groups with various dosages of chitosan-peptide nucleic acid, the animals in the blank control group have greatly swollen lymph nodes and pulmonary carnification; and the PRRSV load in the serum and lymph nodes of pigs in the treatment groups with various dosages of chitosan-peptide nucleic acid (GP5-1+2+M-2+3) is significantly lower than that in the blank control group.

What is claimed is:

1. A peptide nucleic acid, consisting of one or more selected from peptide nucleic acids:
   a) a nucleic acid sequence of Sequence 1 as shown in the Sequencing List of:

5'-AAUAUGAGAGCUGUUGUUGUU-3'; (SEQ ID NO: 1)

b) a nucleic acid sequence of Sequence 2 as shown in the Sequencing List of:

5'-UUAAGUUAUAAAUCAACUGAA-3'; (SEQ ID NO: 2)

c) a nucleic acid sequence of Sequence 3 as shown in the Sequencing List of:

5'-AAUGGAAAACGCCAAAAGCAC-3'; (SEQ ID NO: 3)

and
   d) a nucleic acid sequence of Sequence 4 as shown in the Sequencing List of:

5'-UCAGAAAGAUCAAAAGGUGCA-3'. (SEQ ID NO: 4)

2. The peptide nucleic acid according to claim 1, wherein the peptide nucleic acid is a peptide nucleic acid modified with chitosan.

3. The peptide nucleic acid according to claim 1 is an active ingredient in a peptide nucleic acid formulation.

4. The peptide nucleic acid according to claim 3, wherein the peptide nucleic acid formulation is a colon specific controlled-release microcapsule formulation, injectable lyophilized formulation water-soluble granules for oral use.

5. The peptide nucleic acid according to claim 4, wherein the peptide nucleic acid formulation comprises a pharmaceutically acceptable carrier or excipient.

6. The peptide nucleic acid according to claim 3, wherein the peptide nucleic acid formulation, further comprises a pharmaceutically acceptable carrier or excipient.

7. The peptide nucleic acid according to claim 1 is used in a preparation of a drug for porcine reproductive and respiratory syndrome virus (PRRSV).

* * * * *